(12) United States Patent
Dreher

(10) Patent No.: US 12,115,173 B2
(45) Date of Patent: Oct. 15, 2024

(54) COMPOSITIONS OF HYDROXY ACIDS WITH SALICYLIC ACID AND USES THEREFORE

(71) Applicant: Elba Laboratories, Troy, MI (US)

(72) Inventor: Frank Dreher, San Francisco, CA (US)

(73) Assignee: ELBA LABORATORIES, Troy, MI (US)

( * ) Notice: Subject to any disclaimer, the term of this patent is extended or adjusted under 35 U.S.C. 154(b) by 0 days.

(21) Appl. No.: 17/666,964

(22) Filed: Feb. 8, 2022

(65) Prior Publication Data

US 2022/0249519 A1 Aug. 11, 2022

Related U.S. Application Data

(60) Provisional application No. 63/147,491, filed on Feb. 9, 2021.

(51) Int. Cl.
*A61K 31/616* (2006.01)
*A61K 31/192* (2006.01)
(Continued)

(52) U.S. Cl.
CPC .......... *A61K 31/616* (2013.01); *A61K 31/192* (2013.01); *A61K 31/194* (2013.01);
(Continued)

(58) Field of Classification Search
CPC .............. A61K 2300/00; A61K 9/0014; A61K 31/4172; A61K 38/05; A61K 38/06; A61K 38/07; A61K 8/4946; A61K 8/64; A61K 9/0019; A61K 8/365; A61K 8/02; A61K 8/046; A61K 8/19; A61K 8/28; A61K 8/347; A61K 8/492; A61K 31/375; A61K 8/55; A61K 2800/31; A61K 2800/522; A61K 31/197; A61K 31/198;
(Continued)

(56) References Cited

U.S. PATENT DOCUMENTS 2,533,210 A 12/1950 Baer
2,533,211 A 12/1950 Baer
(Continued)

FOREIGN PATENT DOCUMENTS

DE 102011081434 A1 2/2013
WO WO-2009/011677 A1 1/2009

OTHER PUBLICATIONS

Clear Cell Clear Cell Medicated Acne Masque document, (Published on the internet on Sep. 30, 2020, downloaded from the Internet on Jul. 7, 2023 from https://web.archive.org/web/20200930064001/https://skinboss.care/products/clear-cell-medicated-acne-masque-2oz) (Year: 2020).*

(Continued)

*Primary Examiner* — Savitha M Rao
(74) *Attorney, Agent, or Firm* — Mintz, Levin, Cohn, Ferris, Glovsky and Popeo, P.C.

(57) ABSTRACT

The present disclosure generally relates to topical compositions comprising a combination of at least one alpha-hydroxy acid (e.g., glycolic acid) combined with at least one beta-hydroxy acid (e.g., salicylic acid) in the presence of water-soluble polystyrenes or appropriate salts thereof. The present disclosure further provides methods of making and using such compositions.

15 Claims, 1 Drawing Sheet

(51) Int. Cl.
*A61K 31/194* (2006.01)
*A61K 31/20* (2006.01)
*A61K 31/375* (2006.01)
*A61K 31/60* (2006.01)
*A61K 47/32* (2006.01)

(52) U.S. Cl.
CPC ............ *A61K 31/20* (2013.01); *A61K 31/375* (2013.01); *A61K 31/60* (2013.01); *A61K 47/32* (2013.01)

(58) Field of Classification Search
CPC .. A61K 31/353; A61K 31/355; A61K 31/522; A61K 31/66; A61K 31/685; A61K 31/695; A61K 31/70; A61K 31/715; A61K 31/716; A61K 31/721; A61K 33/30; A61K 33/34; A61K 36/02; A61K 36/04; A61K 36/33; A61K 36/886; A61K 38/00; A61K 45/06; A61K 47/34; A61K 8/44; A61K 8/585; A61K 8/676; A61K 8/678; A61K 8/891; A61K 9/06; A61K 31/19; A61K 31/192; A61K 31/194; A61K 31/20; A61K 31/60; A61K 31/616; A61K 47/32; A61K 8/8117; A61P 17/00; A61P 17/18; A61P 17/02; A61P 15/00; A61P 11/02; A61P 17/06; A61P 17/08; A61P 17/10; A61P 17/12; A61P 29/00; A61P 31/00; A61P 31/10; A61P 33/00; A61P 35/00; A61P 37/08; A61P 39/06; A61P 43/00; A61P 5/28; A61P 1/00; A61Q 19/08; A61Q 5/10; A61Q 19/00; A61Q 19/02; A61Q 19/004
See application file for complete search history.

(56) References Cited

U.S. PATENT DOCUMENTS

| | | | |
|---|---|---|---|
| 2,612,485 A | 9/1952 | Baer | |
| 3,987,163 A | 10/1976 | Rankin | |
| 4,126,142 A * | 11/1978 | Saute | A61K 8/8117 514/159 |
| 4,157,432 A | 6/1979 | Lundberg et al. | |
| 5,547,988 A * | 8/1996 | Yu | A61K 47/26 514/847 |
| 5,840,387 A | 11/1998 | Berlowitz-Tarrant et al. | |
| 6,110,616 A | 8/2000 | Sheikh-Ali et al. | |
| 6,306,419 B1 | 10/2001 | Vachon et al. | |
| 2004/0141936 A1 | 7/2004 | Kropke et al. | |
| 2014/0242130 A1* | 8/2014 | Athwal | A61K 8/9711 424/195.17 |

OTHER PUBLICATIONS

Dermaclear Mask—salicylic acid cream (Allure Labs Inc) Nov. 2020. Located at <https://dailymed.nlm.nih.gov/dailymed/lookup.cfm?setid=9429f477-a916-49c9-bf04-1cf591af5c7f> 4 pages.
International Search Report mailed on May 13, 2022, for PCT Application No. PCT/US2022/015683, filed Feb. 8, 2022, 4 pages.
Peck, R. (Feb. 7, 2019). "Properties Affecting Homogeneity in Semi Solid Manufacturing," located at <https:vxppharma.com/properties-affecting-homogeneity-in-semi-solid-manufacturing> 4 pages.
Ramos-e-Silva, M. et al. (Jul.-Aug. 2001). "Hydroxy acids and retinoids in cosmetics," *Clin Dermatol* 19(4):460-466.
Van Scott, E.J. et al. (Mar.-Apr. 1996). "Alpha-hydroxyacids in the treatment of signs of photoaging," *Clin Dermatol* 14(2):217-226.
Written Opinion mailed on May 13, 2022, for PCT Application No. PCT/US2022/015683, filed Feb. 8, 2022, 4 pages.

* cited by examiner

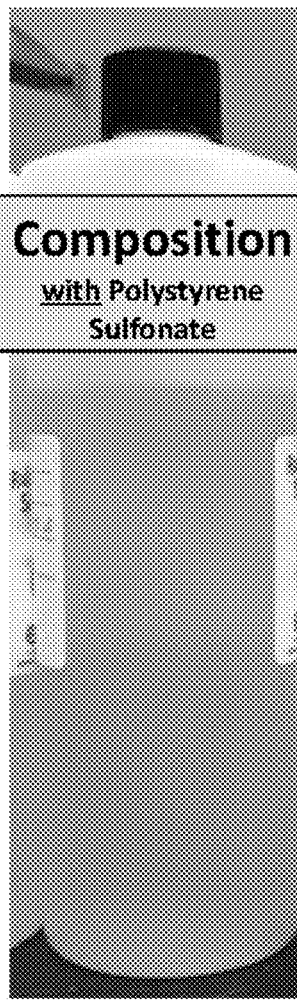
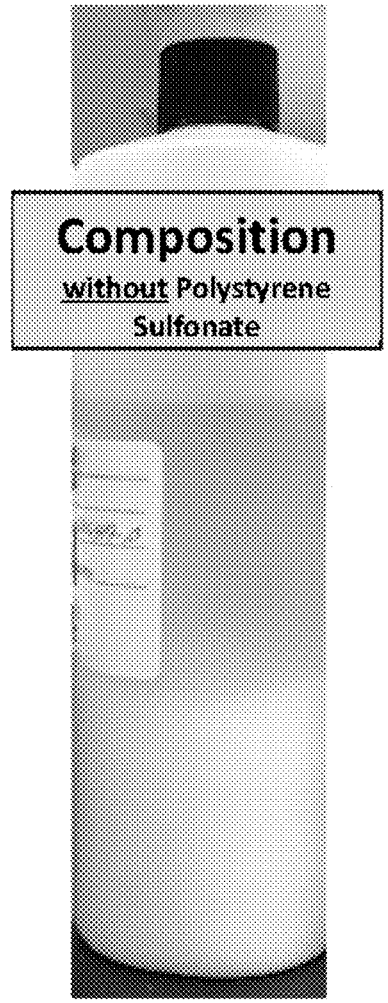

COMPOSITIONS OF HYDROXY ACIDS WITH SALICYLIC ACID AND USES THEREFORE

CROSS REFERENCE TO RELATED APPLICATIONS

This application claims the benefit of and priority to U.S. Provisional Patent Application Ser. No. 63/147,491, filed on Feb. 9, 2021, the entirety of which is incorporated by reference.

FILED OF THE DISCLOSURE

The present disclosure generally relates to topical compositions comprising a combination of at least one alpha-hydroxy acid (e.g., glycolic acid) combined with at least one beta-hydroxy acid (e.g., salicylic acid) in the presence of water-soluble polystyrenes and appropriate salts thereof. The present disclosure further provides methods of making and using such compositions.

BACKGROUND

Both alpha-hydroxy acids and beta-hydroxy acids are useful ingredients for topical compositions, especially when combined in one composition. However, currently available compositions with a combination of alpha-hydroxy acids and beta-hydroxy acids can only contain low concentrations of the two acids. For instance, currently available topical compositions comprising a combination of glycolic acid, an alpha-hydroxy acid, combined with salicylic acid, a beta-hydroxy acid, cannot contain at least 10% (w/w) glycolic acid and at least 5% (w/w) salicylic acid due to technical difficulties in making them in one homogeneous and stable composition effective for the indented use, such as skin peeling.

The present disclosure solves the technical difficulties currently faced by the field by providing compositions comprising higher concentrations of alpha-hydroxy acids and beta-hydroxy acids in the presence of water-soluble polystyrenes in one homogeneous and stable composition suitable for topical use. The present disclosure also provides methods of making and using such compositions.

BRIEF SUMMARY

Provided herein, among others, is a composition comprising at least one alpha-hydroxy acid, at least one beta-hydroxy acid, and one or more water-soluble polystyrene or a salt thereof. In some embodiments, the composition is homogeneous.

In some embodiments, the concentration of the at least one alpha-hydroxy acid is at least about 5% (w/w) to about 40% (w/w). In other embodiments, the concentration of the at least one alpha-hydroxy acid is at least about 7.5% (w/w) to about 30% (w/w).

In some embodiments, the at least one alpha-hydroxy acid comprises 2-hydroxyoctanoic acid, 2-hydroxydecanoic acid, citric acid, glycolic acid, gluconic acid, lactic acid, malic acid, mandelic acid, tartaric acid, or a salt thereof. In some embodiments, the at least one alpha-hydroxy acid comprises glycolic acid or lactic acid.

In some embodiments, the concentration of the at least one beta-hydroxy acid is at least about 2% (w/w) to about 25% (w/w). In certain embodiments, the concentration of the at least one beta-hydroxy acid is about 5% (w/w). In some embodiments, the at least one beta-hydroxy acid comprises salicylic acid, beta-hydroxybutanoic acid, tropic acid, trethocanic acid, and 5-(n-octanoyl) salicylic acid. In certain embodiments, the at least one beta-hydroxy acid comprises salicylic acid.

In some embodiments, the composition has a pH of about 3.5 or lower. In other embodiments, the composition has a pH of about 2.5 or lower.

In some embodiments, the one or more water-soluble polystyrene or a salt thereof comprises an anionic polystyrene and a cationic polystyrene. In some embodiments, the anionic polystyrene comprises a polystyrene sulfonate, a sodium polystyrene sulfonate, or a derivative or salt thereof, and wherein the cationic polystyrene comprises aminomethyl polystyrene or a derivative or salt thereof. In certain embodiments, the water-soluble polystyrene comprises a sodium polystyrene sulfonate.

In some embodiments, the concentration of the one or more water-soluble polystyrene or a salt thereof is in the range of about 0.1% to about 35% (w/w). In other embodiments, the concentration of the one or more water-soluble polystyrene or a salt thereof is in the range of about 1% to about 20% (w/w). In some certain, the concentration of the one or more water-soluble polystyrene or a salt thereof is in the range of about 5% to about 10% (w/w).

In some embodiments, the one or more water-soluble polystyrene or a salt thereof has a molecular weight in the range of about 10,000 to about 1,000,000 g/mol. In other embodiments, the one or more water-soluble polystyrene or a salt thereof has a molecular weight in the range of about 50,000 to about 500,000 g/mol. In certain embodiments, the one or more water-soluble polystyrene or a salt thereof has a molecular weight in the range of about 100,000 to about 200,000 g/mol.

In some embodiments, the composition is liquid to semi-solid. In some embodiments, the composition further comprises ethyl alcohol and water. In some embodiments, the composition is stable.

In other embodiments, the composition further comprises at least one additional hydroxy acid or a salt thereof.

In some embodiments, the at least one additional hydroxy acid or a salt thereof comprises an alpha-hydroxy acid or a salt thereof. In certain embodiments, the alpha-hydroxy acid or a salt thereof comprises a 2-hydroxyoctanoic acid, 2-hydroxydecanoic acid, citric acid, glycolic acid, gluconic acid, lactic acid, malic acid, mandelic acid, tartaric acid, or a salt thereof.

In other embodiments, the at least one additional hydroxy acid or a salt thereof comprises at least one beta-hydroxy acid or a salt thereof. In some embodiments, the beta-hydroxy acid or a salt thereof comprises a beta-hydroxybutanoic acid, a derivative of salicylic acid, or a salt thereof. In some embodiments, the derivative of salicylic acid comprises capryloyl salicylic acid, trethocanic acid, and tropic acid.

In some embodiments, the at least one additional hydroxy acid or a salt thereof comprises a polyhydroxy acid or a salt thereof.

In other embodiments, the composition further comprises an ascorbic acid.

In yet other embodiments, the composition further comprises a non-hydroxy acid. In some embodiments, the non-hydroxy acid comprises kojic acid, amino acids, fatty acids, benzoic acid, retinoic acid, azelaic acid, 4-(2-hydroxyethyl)-1-piperazineethanesulfonic acid, 2-oxothiazoline-4-carboxylic acid (pro-cysteine), pyruvic acid, phytic acid, tranexamic acid, trichloroacetic acid, etidronic acid, dioic acid, and a salt, esters and derivatives, and blends thereof. In certain embodiments, the non-hydroxy acid comprises kojic acid.

In one specific embodiment, the composition comprises about 15% (w/w) of glycolic acid, about 5% (w/w) of salicylic acid, and about 7.5% (w/w) sodium polystyrene sulfonate, wherein the composition has a pH of about 3.0 or lower. In some embodiments, the composition has a pH between about 1.5 and about 2.5.

In another specific embodiment, the composition comprises about 7.5% (w/w) of glycolic acid, about 7.5% (w/w) of lactic acid, about 5% (w/w) of salicylic acid, and about 7.5% (w/w) sodium polystyrene sulfonate, wherein the composition has a pH of about 3.0 or lower. In some embodiments, the composition has a pH between about 1.5 and about 2.5.

In yet another specific embodiment, the composition comprises about 15% (w/w) of glycolic acid, about 5% (w/w) of salicylic acid, about 1% (w/w) of kojic acid, and about 7.5% (w/w) sodium polystyrene sulfonate, wherein the composition has a pH of about 3.0 or lower. In some embodiments, the composition has a pH between about 1.5 and about 2.5.

Also provided herein is a method of making the composition disclosure herein. In some embodiments, the method of making the composition comprises combining at least one alpha-hydroxy acid and at least one beta-hydroxy acid in the presence of one or more water-soluble polystyrene or a salt thereof, and wherein the presence of the one or more water-soluble polystyrene or a salt thereof allows the at least one alpha-hydroxy acid and the at least one beta-hydroxy acid to be combined in one homogeneous composition suitable for topical use. In other embodiments, the method of making the composition further comprises combining the at least one alpha-hydroxy and the one or more water-soluble polystyrene or a salt thereof prior to combining the at least one alpha-hydroxy acid and the at least one beta-hydroxy acid. In certain embodiments, the at least one alpha-hydroxy acid and the at least one beta-hydroxy acid are combined at a pH of about 3.0 or lower.

Further provided herein is a method of improving a skin condition in a subject in need thereof comprising applying the composition disclosure herein on an area of the skin. In some embodiments, the skin condition to be improved comprises aging, color, texture of the skin. In other embodiments, the skin condition comprises acne, folliculitis or pseudo-folliculitis, seborrheic dermatitis, rosacea, hyperkeratosis, actinic keratosis, and a skin cancer.

BRIEF DESCRIPTION OF THE DRAWINGS

FIG. 1 is an exemplary demonstration of the compositions described herein. In particular, a composition on the right is made without the sodium polystyrene sulfonate, where the sodium polystyrene sulfonate is replaced with water. As can be seen, this composition is not homogeneous, showing clear phase separation. The composition cannot be stable and homogeneous, and at the same time, also have a low pH (e.g., below a pH of about 3.0). Accordingly, this composition is not effective. Such a composition is not in accordance to the present disclosure. Unexpectedly and in contrast, the composition on the left is a homogeneous composition according to this present disclosure. In particular, the composition is made with the sodium polystyrene sulfonate (i.e., FLEXAN® II Polymer). The composition is stable, homogeneous, and at the same time, of low pH (e.g., below a pH of about 3.0), and is therefore effective.

DETAILED DESCRIPTION OF THE DISCLOSURE

The present disclosure relates to compositions comprising a combination of at least one alpha-hydroxy acid (such as glycolic acid) combined with at least one beta-hydroxy acid (such as salicylic acid) in the presence of water-soluble polystyrenes and appropriate salts thereof (e.g., sodium polystyrene sulfonate) of an appropriate molecular weight range for water-solubility. The present disclosure further relates to methods of using the compositions for various non-pathologic and pathologic skin conditions in a subject. The present disclosure also provides methods of making the compositions.

Furthermore, the compositions of the present disclosure can be applied in improving various non-pathological skin conditions, for example, skin smoothing, roughness improving, skin exfoliating, skin lightening, skin tone improving, skin pore refining, and/or skin rejuvenating. The compositions of the present disclosure can also be used in the treatment of various skin conditions including, but not limited to, acne, folliculitis or pseudo-folliculitis, seborrheic dermatitis, rosacea, hyperkeratosis, actinic keratosis, and skin cancer.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

As used herein, a "subject" or an "individual" includes animals, such as human (e.g., human individuals) and non-human animals. In some embodiments, a "subject" or "individual" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. In some embodiments, the term "about" indicates the designated value ±up to 10%, up to ±5%, or up to ±1%.

It is understood that aspects and embodiments of the disclosure described herein include "comprising", "consisting", and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Headings, e.g., (a), (b), (i) etc., are presented merely for ease of reading the specification and claims. The use of headings in the specification or claims does not require the steps or elements be performed in alphabetical or numerical order or the order in which they are presented.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, the use of these terms in the specification does not by itself connote any required priority, precedence, or order.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Compositions of the Disclosure

One aspect of the present disclosure relates to compositions comprising certain concentrations of at least one alpha-hydroxy acid, at least one beta-salicylic acid, and one or more water-soluble polystyrene or a salt thereof and have low pH (e.g., generally about 4 or lower). The compositions provided herein are generally homogeneous and stable as described in more detail below.

Hydroxy acids are known in the art, and can generally be divided into four subfamilies: alpha-hydroxy acids, beta-hydroxy acids, alpha- and beta-hydroxy acids, and polyhydroxy acids. Alpha-hydroxy acids are frequently used in topical compositions, such as for skin care products, as they are among the most useful exfoliation agents. Beta-hydroxy acids are generally used in skin care products. They can be useful skin exfoliation agents and can help against acne or other skin conditions and disorders. Alpha-beta-hydroxy acids contain at least one alpha-hydroxy acid group and one beta-hydroxy acid group. Non-limiting examples of alpha-beta-hydroxy acids include: malic acid, citric acid, and tartaric acid. A final member of the hydroxy acid family is the polyhydroxy acid, which, as the name suggests, are molecules having at least one carboxylic acid functional group and more than one hydroxyl group. Polyhydroxy acids may be naturally occurring or synthetically manufactured, and have a higher molecular weight than glycolic acid or lactic acid. As a result, polyhydroxy acids are generally less skin penetrating than these two alpha-hydroxy acids, and, as a result, provide gentler skin effects, typically with reduced irritation. Examples of suitable polyhydroxy acids include lactobionic acid and gluconic acid. All of the hydroxy acids are contemplated by the present disclosure, and are discussed in more detail herein.

In general, alpha-hydroxy acids possess a carboxylic acid group (—COOH) with a hydroxyl group (—OH) on the adjacent carbon atom of the molecule. Many alpha-hydroxy acids are generally known in the field and are all contemplated by the present disclosures. Both naturally occurring and synthetic alpha-hydroxy acids are known and suitable for use in the disclosure. Some non-limiting exemplary alpha-hydroxy acids that can be used in the compositions provided herein include, without being limited to, 2-hydroxyoctanoic acid, 2-hydroxydecanoic acid, citric acid, glycolic acid, gluconic acid, lactic acid, malic acid, mandelic acid, tartaric acid, or a salt thereof. In some embodiments, the alpha-hydroxy acids used herein are those exhibiting high epidermis penetration so that they may exert a maximum effect on the underlying dermis layer. For instance, some examples of effective alpha-hydroxy acids are those with small molecular weight, such as glycolic acid and lactic acid. However, alpha-hydroxy acids with higher molecular weight are also compatible with the present disclosure and are therefore encompassed herein. In one embodiment, the at least one alpha-hydroxy acid is a glycolic acid. In another embodiment, the at least one alpha-hydroxy acid is a lactic acid.

The compositions provided herein can contain the at least one alpha-hydroxy acid at a weight concentration of up to about 50% (w/w). In some embodiments, the concentration of the at least one alpha-hydroxy acid in the compositions is at least about 5% (w/w) to about 40% (w/w). In other embodiments, the concentration of the at least one alpha-hydroxy acid in the compositions is at least about 7.5% (w/w) to about 30% (w/w). In some embodiments, the concentration of the at least one alpha-hydroxy acid in the compositions is at least about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), or about 20% (w/w). In other embodiments, the concentration of the at least one alpha-hydroxy acid in the compositions is at least about 25% (w/w), about 30% (w/w), about 35% (w/w), about 40% (w/w), about 45% (w/w), or about 50% (w/w).

The compositions provided herein also contain at least one beta-hydroxy acid. Beta-hydroxy acids generally refers to molecules having a carboxylic acid group (—COOH) and a hydroxyl group (—OH) separated by two carbon atoms. Many beta-hydroxy acids are generally known in the field and are all contemplated by the present disclosures. Thus, both naturally occurring and synthetic beta-hydroxy acids are known and may be used in the disclosure's compositions. Some non-limiting exemplary beta-hydroxy acids that can be used in the compositions provided herein include, without being limited to, salicylic acid, beta-hydroxybutanoic acid, tropic acid, trethocanic acid, and 5-(n-octanoyl) salicylic acid (also known as capryloyl salicylic acid) and other derivatives of salicylic acid. In one exemplary embodiment, the at least one beta-hydroxy acid is a salicylic acid.

The compositions provided herein can contain the at least one beta-hydroxy acid at a weight concentration of up to about 25% (w/w). In some embodiments, the concentration of the at least one beta-hydroxy acid in the compositions is at least about 2% (w/w) to about 25% (w/w). In other embodiments, the concentration of the at least one beta-hydroxy acid in the compositions is at least about 5% (w/w) to about 25% (w/w). In some embodiments, the concentration of the at least one beta-hydroxy acid in the compositions is at least about 2% (w/w), about 3% (w/w), about 4% (w/w), about 4.5% (w/w), about 4.6% (w/w), about 4.7% (w/w), about 4.8% (w/w), about 4.9% (w/w), about 5% (w/w), about 5.1% (w/w), about 5.2% (w/w), about 5.3% (w/w), about 5.4% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), or about 10% (w/w). In other embodiments, the concentration of the at least one beta-hydroxy acid in the compositions is at least about 11% (w/w), about 12% (w/w), about 13% (w/w), about 14% (w/w), about 15% (w/w), about 16% (w/w), about 17% (w/w), about 18% (w/w), or about 19% (w/w). In one exemplary embodiment, the concentration of the at least one beta-hydroxy acid in the compositions is about 5% (w/w).

Topical compositions comprising at least one hydroxy acid (such as glycolic acid) combined with at least one beta-hydroxy acid (such as salicylic acid) only contain low concentrations of the two acids. More specifically, topical compositions comprising a combination of glycolic acid combined with salicylic acid do not contain both at least 10% (w/w) glycolic acid and at least 5% (w/w) salicylic acid in one homogeneous (e.g., single phase) and stable (e.g., does not phase separate with time) liquid to semi-solid composition suitable for topical use. Unexpectedly, as disclosed herein, the use of water-soluble polystyrenes and appropriate salts thereof allows the combination of both acids at higher concentrations (e.g., glycolic acid of at least 10% (w/w) and salicylic acid of at least 5% (w/w)) in one homogeneous and stable composition suitable for topical use. In some embodiments, the composition can be liquid to semi-solid. Without being bound by theories, the present disclosure demonstrates that, in some instances, the inclusion of water-soluble polystyrenes in the compositions provide water-solubility.

The water-soluble polystyrenes encompassed herein can be anionic polystyrenes and cationic polystyrenes, or derivatives thereof. A derivative of the water-soluble polystyrene as disclosed herein generally refers to a compound that is formed from a water-soluble polystyrene described herein or a compound that can be imagined to arise from a water-soluble polystyrene described herein. A salt of a water-soluble polystyrene as disclosed herein generally refers to a water-soluble polystyrene in its salt form. Anionic polystyrenes have cations (positively charged ions) as their counter ions. Cationic polystyrenes have anions (negatively charged ions) as their counter ions. A counter ion is the ion that accompanies an ionic species in order to maintain electric neutrality. For example, sodium ion ($Na^+$) is a frequent counter ion of anionic polystyrenes. Potassium ion ($K^+$), magnesium ion ($Mg^{2+}$), calcium ion ($Ca^{2+}$), ammonium ion ($NH_4^+$), and ammonium derivatives where the hydrogen atoms in the ammonium ion are substituted with an alkyl group or some other organic group, are other examples of common counter ions of anionic polystyrenes. For example, without being limited to, counter ions for cationic polystyrenes can be chloride ($Cl^-$), fluoride ($F^-$), bromide ($Br^-$), acetate ($CH_3CO_2^-$), or sulfate ($SO_4^{2-}$).

Non-limiting exemplary anionic polystyrenes include, without being limited to, polystyrene sulfonates and sodium polystyrene sulfonates, or derivatives and/or salts thereof. Non-limiting exemplary cationic polystyrene include, without being limited to, aminomethyl polystyrene, or derivatives and/or salts thereof.

As used herein, the term "polystyrene sulfonate" generally refers to the class of polymers which is characterized by the polymerization of alkenyl aromatic sulfonates or the sulfonation of polymers of alkenyl aromatics. Accordingly, the term "polystyrene sulfonate" as used herein is not limited to the literal polystyrene sulfonates but is also inclusive of copolymers of styrene sulfonate and homopolymers and copolymers of styrene sulfonate analogs. It is also intended that the wide variety of polymers produced by sulfonation of alkenyl aromatic containing polymers be included as well. Thus, the polystyrene sulfonate polymers described herein encompasses a class of polymers, many variations of which are commercially available. The polymerization techniques for the preparation of such materials are similarly known to those of ordinary skill in the art and many variations of such techniques are similarly in practice in commerce. Polystyrene sulfonates are generally freely soluble in water without degradation. Polystyrene sulfonates with wide ranges of molecular weights are available. Some embodiments of ranges of molecular weights for the polystyrene sulfonates used in the present disclosure are described in more detail below. In certain embodiments of the present disclosure, the water-soluble polystyrene can be sodium polystyrene sulfonate. The polystyrene sulfonate sold under the trade-name of FLEXAN® II Polymer by AkzoNobel is an example of such a water-soluble polystyrene.

Polystyrene sulfonate polymers suitable for use in this disclosure can be synthesized in different ways, including any synthesis strategies and methods currently available or to be developed. Generally, for example, sodium polystyrene sulfonate may be produced by sulfonating polystyrene and neutralizing the resultant polystyrene with sodium hydroxide or, alternatively, by sulfonating styrene monomer, polymerizing, then neutralizing the resultant product. Furthermore, without being limiting, methods and processes described in U.S. Pat. Nos. 2,533,210; 2,533,211; 2,612,485; 3,987,163; 4,157,432; 5,840,387; 6,110,616; and 6,306,419 (the entire contents of all of which are incorporated herein by reference) may be also used, combined, and/or modified in order to obtain various polystyrene sulfonate polymers which are water-soluble and suitable for the present disclosure.

Generally, cationic polystyrenes may be used instead of anionic polystyrenes, such as the polystyrene sulfonate polymers and salts thereof described herein. Accordingly, under certain circumstances, water soluble cationic polystyrenes, and suitable derivatives and/or salts thereof are also suitable for the present disclosure. In certain exemplary embodiments of the present disclosure, the cationic polystyrene can be aminomethyl polystyrenes.

The one or more water-soluble polystyrenes encompassed herein (e.g., polystyrene sulfonates and sodium polystyrene sulfonates) can have certain appropriate molecular weight ranges. In some embodiments, the one or more water-soluble polystyrene or a salt thereof has a molecular weight in the range of about 5,000 to about 2,000,000 grams per mole (g/mol). In some embodiments, the one or more water-soluble polystyrene or a salt thereof has a molecular weight in the range of about 10,000 to about 1,000,000 g/mol. In some embodiments, the one or more water-soluble polystyrene or a salt thereof has a molecular weight in the range of about 20,000 to about 900,000 g/mol. In some embodiments, the one or more water-soluble polystyrene or a salt thereof has a molecular weight in the range of about 30,000 to about 800,000 g/mol. In some embodiments, the one or more water-soluble polystyrene or a salt thereof has a molecular weight in the range of about 40,000 to about 700,000 g/mol. In some embodiments, the one or more water-soluble polystyrene or a salt thereof has a molecular weight in the range of about 45,000 to about 600,000 g/mol. In other embodiments, the one or more water-soluble polystyrene or a salt thereof has a molecular weight in the range of about 50,000 to about 500,000 g/mol. In certain embodiments, the one or more water-soluble polystyrene or a salt thereof has a molecular weight in the range of about 100,000 to about 200,000 g/mol.

Without being bound by theories, polystyrene sulfonates can have extraordinary thickening effect in water, even in the presence of salts. The thickening power can increase sharply with both concentration and molecular weight. In addition, polystyrene sulfonates may act as lubricants. Generally, without being bound by theories, a polystyrene sulfonate with a higher molecular weight produces a lubricating film with higher strength in solutions due to the orientation of polymer molecules.

The concentration of the one or more water-soluble polystyrene or a salt thereof (e.g., polystyrene sulfonates and sodium polystyrene sulfonates) of the present disclosure can vary. For example, it may vary depending on the molecular weight of the polystyrene sulfonate. Further, it may vary depending on the concentrations of both the alpha-hydroxy acid (e.g., glycolic acid) and beta-hydroxy acid (e.g., the salicylic acid). In certain embodiments, the concentration of the one or more water-soluble polystyrene may vary to provide a viscosity up to about 50,000 cps at 25° C. as measured by a viscometer (e.g., a Brookfield Dial Reading Viscometer). If a composition of higher viscosity is desired, such a composition may be obtained by adding additional suitable chemicals with thickening properties (e.g., rheology modifiers) which are compatible with composition containing more concentrated acids.

The concentration of the polystyrene in the composition is critical for the present disclosure. In some embodiments, as mentioned above, the concentration of the polystyrene in the composition can vary depending upon the molecular weight of the water-soluble polystyrene or a salt thereof (e.g., polystyrene sulfonates and sodium polystyrene sulfonates) employed and/or the concentration of the acids (i.e., salicylic acid combined with at least one alpha-hydroxy acid). In some embodiments, the concentration of the one or more water-soluble polystyrene or a salt thereof must be of at least a certain minimal level in order to obtain the compositions described herein (e.g., a composition containing at least one alpha-hydroxy acid of at least 10% (w/w) combined with salicylic acid of at least 5% (w/w) in one homogeneous (e.g., single phase) and stable (e.g., does not phase separate with time) liquid to semi-solid composition which is suitable for topical use and is also effective).

For instance, in some embodiments, the concentration of the one or more water-soluble polystyrene or a salt thereof can be in the range of about 0.1% to about 35% (w/w). In other embodiments, the concentration of the one or more water-soluble polystyrene or a salt thereof can be in the range of about 0.5% to about 30% (w/w). In some embodiments, the concentration of the one or more water-soluble polystyrene or a salt thereof can be in the range of about 1% to about 20% (w/w). In other embodiments, the concentration of the one or more water-soluble polystyrene or a salt thereof can be in the range of about 2% to about 18% (w/w), about 3% to about 16% (w/w), or about 4% to about 14% (w/w). In certain embodiments, the concentration of the one or more water-soluble polystyrene or a salt thereof can be in the range of about 5% to about 10% (w/w). It is understood that any numbers between the recited ranges are also encompassed. In one embodiment, the concentration of the one or more water-soluble polystyrene or a salt thereof is at least about 5% (w/w). In another embodiment, the concentration of the one or more water-soluble polystyrene or a salt thereof is at least about 5.5% (w/w). In one embodiment, the concentration of the one or more water-soluble polystyrene or a salt thereof is at least about 6% (w/w). In one embodiment, the concentration of the one or more water-soluble polystyrene or a salt thereof is about at least 6.5% (w/w). In another embodiment, the concentration of the one or more water-soluble polystyrene or a salt thereof is at least about 7% (w/w). In a specific embodiment, the concentration of the one or more water-soluble polystyrene or a salt thereof is at least about 7.5% (w/w). In another embodiment, the concentration of the one or more water-soluble polystyrene or a salt thereof is at least about 8% (w/w). In yet other embodiments, the concentration of the one or more water-soluble polystyrene or a salt thereof is at least about 8.5% (w/w), about 9% (w/w), or about 9.5% (w/w).

For example, without limiting the scope of this disclosure, such a composition can be obtained when mixing about 7.5% (w/w) sodium polystyrene sulfonate of a molecular weight of about 100,000 to 200,000 g/mol (e.g., FLEXAN® II Polymer by AkzoNobel) with about 15% (w/w) glycolic acid and about 5% (w/w) salicylic acid in a mixture of water and ethanol. Such a composition forms a pH of less than 3.0. In another embodiment, without limiting the scope of this disclosure, such a composition can be obtained when mixing about 7.5% (w/w) sodium polystyrene sulfonate of a molecular weight of about 100,000 to 200,000 g/mol (e.g., FLEXAN® II Polymer by AkzoNobel) with about 15% (w/w) glycolic acid and about 5% (w/w) salicylic acid in a mixture of about 42.5% (w/w) water and about 30% (w/w) ethanol (e.g., ethyl alcohol 200 proof). In some embodiments, the compositions form a pH of between about 2.0 to about 2.5.

Alpha and beta-hydroxy acids (such as glycolic acid and salicylic acid) are known to be more effective for skin in their acid forms as compared to their deprotonated (i.e., dissociated) forms. This has been well recognized. Therefore, the compositions in accordance to this disclosure provides higher efficiency for improving a skin condition (e.g., better exfoliating properties, better skin smoothing, better skin lightening, more active against acne, etc.) as compared to a composition at a higher pH, such as at a pH higher than the pKa of the acid with the lowest pKa in the composition.

The use of water-soluble polystyrenes and appropriate salts thereof (such as sodium polystyrene sulfonate of an appropriate molecular weight range for water-solubility) allows the combination of both hydroxy acids at certain concentrations, e.g., glycolic acid of at least 10% (w/w) and salicylic acid of at least 5% (w/w), in one homogeneous and stable liquid to semi-solid composition suitable for topical use at a low pH. For the purpose of the present disclosure, a low pH is defined as a pH of a composition of the present disclosure where the hydroxy acids, such as glycolic acid and the salicylic acid, are present at 50% or higher in their acid forms. In other words, the acid form is the form where the respective carboxy acid (—COOH) of the acid is not deprotonated (i.e., in the dissociated form —COO$^-$). The acid form of an acid is generally present at a ratio of at least 50% at the pH of a composition equal to or lower than the pKa of the acid, with the rest of the acid is in its deprotonated form. For instance, the pKa of glycolic acid is about 3.8 and the pKa of salicylic acid is about 3.0.

Thus, in some embodiments, the composition has a pH of about 4 or lower. In other embodiments, the composition has a pH of about 3.9, about 3.8, about 3.7, about 3.6, about 3.5, about 3.4, about 3.3, about 3.2, about 3.1, about 3, about 2.9, about 2.8, about 2.7, about 2.6, or lower. In some embodiments, the composition has a pH of about 2.5 or lower. In some embodiments, the composition provided herein has a pH between about 1.0 and about 3. In certain embodiments, the composition provided herein has a pH between about 1.5 and about 2.5.

As a non-limiting example of the present disclosure, the composition can comprise a combination of glycolic acid of at least about 10% (w/w) and salicylic acid of at least about 5% (w/w) in one homogeneous and stable liquid to semi-solid composition suitable for topical use, and has a pH of about 3.0 or lower. In such an embodiment, at least about 50% of both glycolic acid and salicylic acid are in their respective acid form.

It is generally known that acidic personal and pharmaceutical compositions elicit special responses when applied topically to skin. More particularly, without being bound by theories, in contrast to higher pH compositions, compositions with hydroxy acids or similar acids and with lower pH used for skin treatments offer beneficial effects, such as, without being limited to, an increase in epidermis exfoliation to alleviate skin conditions (e.g., hyperkeratosis, dry/flaky/itchy skin, etc.), enhance miniaturization, minimize the appearance of lines and wrinkles, increase dermal thickness, increase anti-acne benefits, and increase dermal perfusion (e.g., vascular effects). In contrast, compositions containing the same acids but having higher pH do not offer, or offer to a lesser extent, the aforementioned benefits. A review of these actions as related to a particular type of acids, i.e., hydroxy acids, is provided in "Hydroxy Acids and Retinoids in Cosmetics," Clinics in Dermatol., 2001; 19: 460-466, which is hereby incorporated herein in its entirety by reference. Also, an instructive review of alpha hydroxy acids, including the types, mechanisms of action, formulations, and treatment results, is provided in "Alpha-Hydroxyacids in the Treatment of Signs of Photoaging," Clinics in Derma., 1996; 14: 217-226, which also is incorporated herein in its entirety by reference. This article recognizes pHs in the range from about 0.6 to about 4.0. However, this article does not describe how alpha-hydroxy acids can be combined with beta-hydroxy acids, such as salicylic acid, as described herein.

While low pH topical compositions can provide useful benefits to the consumer, they can pose real challenges to the formulation scientists, production staff, and even the consumers. It is well appreciated by one skilled in the art that low pH compositions can be difficult to maintain homogeneous and stable. However, the compositions provided herein have low pH and are substantially homogeneous and stable.

A substantially "homogeneous" composition as used herein refers to compositions that are essentially uniform throughout the entire composition. The uniformity of a composition can be demonstrated by methods and assays generally known in the art, including without being limited to, visual inspection, pH, density (i.e., weight per unit volume, such as grams per cm$^3$) and chemical analysis. For instance, a composition provided herein has the same pH throughout, i.e., samples taken from the top, the middle, and the bottom of the composition should have approximately the same pH. Additionally, a composition which is a mixture, such as the compositions of the present disclosure, should have a uniform and definite constitution throughout, i.e., samples taken from the top, the middle, and the bottom of the composition should have approximately the same concentrations of each constituent. In other embodiments, the composition exhibits homogeneous or uniform viscosity throughout.

Thus, in some embodiments, any parameters (such as pH values, concentration of constituents, viscosity, etc.) for samples taken from various parts of a homogeneous composition differ no more than about ±10%. In some specific embodiments, any parameters for samples taken from various parts of a homogeneous composition differ no more than about ±10%. In other embodiments, if any parameters (such as pH values, concentration of constituents, viscosity, etc.) for samples taken from various parts of a composition differ significantly, e.g., by more than about ±10%, then the composition is not homogeneous. In certain embodiments, if any parameters for samples taken from various parts of a composition differ by more than about ±10%, the composition is not homogeneous.

Furthermore, the homogeneity of a composition can be inspected visually. In some embodiments, the compositions should exhibit homogeneous or uniform color and/or clarity throughout. In other embodiments, the homogeneous compositions provided herein should be generally in a single phase. A composition showing physical separation is not uniform or homogeneous. In certain embodiments, the compositions provided herein appear to be mostly clear to slightly opaque and yellowish to brownish liquid. In some embodiments, the compositions provided herein appear to be yellowish to brownish semi-solid. In other embodiments, the homogeneous compositions provided herein are generally in a continuous phase. In certain embodiments, the compositions provided herein are completely homogeneous.

In addition to being homogeneous, the compositions provided herein are also stable under normal storage conditions typical for cosmetic and/or dermatology products as described herein. In some embodiments, the compositions provided herein are physically and chemically stable. In general, a physically stable composition means that the composition does not phase separate over time under normal storage conditions. A chemically stable composition means that the chemical properties of the composition and the constituents of a composition do not significantly change (e.g., concentration of active ingredients remains constant and within concentration range of about ±10%) over time under normal storage conditions.

The normal storage conditions typical for cosmetic and/or dermatology products encompassed herein include, without being limited to, storage at suitable temperatures, being kept in bathroom at home, being kept in skin care/medical cabinet. The suitable temperatures can include, without being limited to, a temperature between about 4° C. and about 30° C. In some embodiments, a suitable temperature can be about 18° C., about 20° C., or about 25° C. In other embodiments, a suitable temperature can be between about 18° C. to about 25° C.

The compositions provided here can also remain homogeneous and stable in a moist environment that resembles, for example, the bathroom in a home. In other embodiments, the compositions provided here can also remain homogeneous and stable during normal commercial transportation, with or without refrigeration, and during the storage at a warehouse or a store.

In other embodiments, the compositions provided here can be kept in an appropriate closed container. Some non-limiting examples include plastic or glass jars, plastic or glass bottles, special glass containers, or cosmetic dispensers.

The compositions provided here can be stored for a prolonged period of time while remain homogeneous and stable. For example, the compositions provided here can be stored for 6 months, 1 year, 2 years, 3 years, or up to 5 year under the conditions as described herein, while remain homogeneous and stable.

In some specific embodiments, a composition provided herein presents as a mostly clear to slightly opaque, yellowish to brownish, and homogeneous liquid. The composition remains stable (i.e., in terms of appearance, pH range, homogeneity, viscosity) over a prolonged period of time (i.e., at least for 2 years) when kept in an appropriate closed container under normal storage condition typical for cosmetic and/or dermatology products as described herein.

The compositions of the present disclosure can also include at least one additional hydroxy acid or a salt thereof as described herein. In some embodiments, the at least one additional hydroxy acid or a salt thereof can be an alpha-hydroxy acid or a salt thereof as described herein. In some embodiments, the at least one additional alpha-hydroxy acid can be lactic acid, 2-hydroxyoctanoic acid, 2-hydroxydecanoic acid, citric acid, gluconic acid, malic acid, mandelic acid, tartaric acid, or a salt thereof. In some embodiments, the at least one additional hydroxy acid or a salt thereof can be at least one beta-hydroxy acid or a salt thereof as described herein. For instance, the at least one additional beta-hydroxy acid or a salt thereof can be beta-hydroxybutanoic acid, trethocanic acid, tropic acid, a derivative of salicylic acid, or a salt thereof. In certain embodiments, the derivative of salicylic acid can be capryloyl salicylic acid. In some embodiments, the at least one additional hydroxy acid or a salt thereof can be a polyhydroxy acid or a salt thereof as described herein.

In other aspects, the compositions of the present disclosure can also include a non-alpha-, non-beta-, or non-polyhydroxy acid as disclosed here. Some non-limiting examples of such acids include ascorbic acid, kojic acid, amino acids, fatty acids, benzoic acid, retinoic acid, azelaic acid, 4-(2-hydroxyethyl)-1-piperazineethanesulfonic acid, 2-oxothiazoline-4-carboxylic acid (pro-cysteine), pyruvic acid, phytic acid, tranexamic acid, acetic acid, trifluoroacetic acid, hydrochloric acid, trichloroacetic acid, etidronic acid, dioic acid, and a salt, esters and derivatives, and blends thereof. In one embodiment, the non-alpha-, non-beta-, or non-polyhydroxy acid is kojic acid.

In still other aspects, the present disclosure can use a mixture of water and ethyl alcohol as solvents. However, it is understood that other appropriate solvents or co-solvents with comparable properties (to water and/or ethyl alcohol) may also be used. Non-limiting exemplary solvents or co-solvents include denatured ethyl alcohol, isopropyl alcohol, propylene glycol, propanediol, glycerin, low molecular weight and water soluble polyethylene glycols, etc., and their mixtures with or without water and/or ethyl alcohol. A skilled person in the art, such as a formulation chemist, pharmacist, or scientists with expertise in the preparation of cosmetic and dermatological formulations suitable for human use, would know how to choose suitable solvents or co-solvents.

The compositions provided herein can be liquid to semi-solid. As used herein, a semi-solid composition generally refers to composition that is in between a solid and a liquid. Another name for a semi-solid is a quasi-solid. A semi-solid composition does not hold its shape like a solid but does not flow like a liquid. For instance, a cream (e.g., face cream, hand cream, or body cream) is an example of a semi-solid. A substance like gel or cream is another example of a semi-solid. In some embodiments, the compositions provided herein may be formulated in types of, for example, cream, lotion, oil, paste, powder, essence, beauty wash, pack, gel, spray, ointment, emulsion, etc. In addition, the compositions provided herein may be prepared into various products such as cream, cleanser, body wash, lipstick, cosmetics for hair (for example, shampoo, rinse, essence, etc.), hand cream, foundation, etc.

A further object of the present disclosure is the provision of such compositions which can be readily modified. Such modifications include the addition of chemicals which are compatible with hydroxy acids, such as glycolic acid combined with salicylic acid, in the presence of water-soluble polystyrenes and appropriate salts thereof (such as sodium polystyrene sulfonate with an appropriate molecular weight range for water-solubility) and which are suitable for topical use for skin. Non-limiting exemplary chemicals can be actives in a dermatological product (such as cosmetic actives, OTC drug actives, dermatology drug actives, active pharmaceutical ingredients, biopharmaceuticals, biologics, and dietary supplements), solvents or co-solvents, rheology modifiers, preservatives, pH adjusters, emollients, surfactants, occlusive agents, moisturizers, humectants, natural moisturizing factors, stabilizers, antioxidants, UV-absorbing chemicals, sunscreens, fatty acids, lipids, amino acids, peptides, proteins, pearling agents, fragrances, color additives, film-forming agents, foaming agents, polymers (natural and synthetic, including but not limited to, polysaccharides, glycosaminoglycans, polyethylene glycols, polypropylene glycols, polyvinylpyrrolidones, etc.), skin delivery modifying agents (skin penetration enhancers, skin penetration retarders, controlled release systems, . . . ), cleansing agents, hair-styling agents, particles (of any shape/form and dimension suitable in the present disclosure), micro-RNA, RNA, DNA, enzymes, natural extracts, natural oils, microbes, cells, cell fragments, cell lysates, conditioned cell media, and their appropriate combinations; as known by a skilled person in the art.

Moreover, the composition in accordance to this disclosure can additionally contain one or more cosmetic active and/or drug active including but not limited to skin depigmentation or lightening actives, skin brightening actives, anti-inflammatory agents, anti-histamines, antimicrobials, exfoliants, keratolytics, anti-acne actives, hair growth actives, anti-hair loss actives, pro-biotics, post-biotics, skin barrier agents, skin protectants, skin rejuvenating actives, myorelaxants, collagen/elastin-stimulating actives, peroxisome proliferation activators, protease activation receptor agonists, lipids, sex hormones, sunscreen, vitamins, growth factors, cytokines, enzymes, retinoids, vasoconstrictors, or any other topical OTC/dermatology drugs and/or their respective pro-drugs, and their appropriate combinations, as known by a skilled person in the art. Other personal care acids and pharmaceutical acids are known and are contemplated for use in the compositions of the disclosure.

As described in more detail below, one exemplary composition of the present disclosure contains about 15% (w/w) of glycolic acid, about 5% (w/w) of salicylic acid, and about 7.5% (w/w) sodium polystyrene sulfonate, and the composition has a pH of about 3.0 or lower. Another exemplary composition of the present disclosure contains about 7.5% (w/w) of glycolic acid, about 7.5% (w/w) of lactic acid, about 5% (w/w) of salicylic acid, and about 7.5% (w/w) sodium polystyrene sulfonate, and the composition has a pH of about 3.0 or lower. Still another exemplary composition of the present disclosure contains about 15% (w/w) of glycolic acid, about 5% (w/w) of salicylic acid, about 1% (w/w) of kojic acid, and about 7.5% (w/w) sodium polystyrene sulfonate, wherein the composition has a pH of about 3.0 or lower. In certain embodiments, the compositions of the present disclosure have a pH between about 1.5 and about 2.5.

Methods of the Disclosure

The present disclosure further provides a method of making the composition described herein. The method generally comprises combining at least one alpha-hydroxy acid and at least one beta-hydroxy acid in the presence of one or more water-soluble polystyrene or a salt thereof, as described herein. The presence of the one or more water-soluble polystyrene or a salt thereof allows the alpha-hydroxy acid and the beta-hydroxy acid to be combined in one homogeneous composition suitable for topical use.

In some embodiments, the at least one alpha-hydroxy acid and the at least one beta-hydroxy acid are combined at a pH of about 3.0 or lower. Other suitable ranges of pH are described in above sections. As provided by the present disclosure, such a low pH can be generally obtained when combining water-soluble polystyrenes and appropriate salts thereof (such as sodium polystyrene sulfonate of an appropriate molecular weight range for water-solubility) with both at least 10% (w/w) of an alpha-hydroxy acid (such as glycolic acid) and at least 5% (w/w) of a beta-hydroxy acid (such as salicylic acid) in a mixture of water and ethyl alcohol. In some embodiments, the pH formed by combing the two acids with water and ethyl alcohol can be the spontaneous pH of the composition. In some embodiments, a lower pH (e.g., a pH lower than about 3.0) may be obtained when additional acids (e.g., hydrochloric acid) are combined with the composition. In accordance to the present disclosure, as a result of the use of water-soluble polystyrenes and appropriate salts thereof (such as sodium polystyrene sulfonate of an appropriate molecular weight range for water-solubility), a stable and homogeneous liquid to semi-solid composition can be obtained without the need to adjust the pH with an alkaline chemical (e.g., aqueous solution of sodium hydroxide, etc.).

In some embodiments, the use of water-soluble polystyrenes and appropriate salts thereof (such as sodium polystyrene sulfonate of an appropriate molecular weight range for water-solubility) allows for the preparing a liquid to semi-solid compositions comprising both alpha- and beta-hydroxy acids at certain concentrations as described herein (e.g., at least 10% (w/w) glycolic acid and at least 5% (w/w) salicylic acid) in a mixture of water and ethyl alcohol at spontaneous pH which is suitable for topical use. The resulting composition is homogeneous, stable, and also effective for skin use.

In some embodiments, the method of making the composition comprises combining the at least one alpha-hydroxy acid and the one or more water-soluble polystyrenes or salts thereof prior to combining the at least one alpha-hydroxy acid and the at least one beta-hydroxy acid. Some exemplary embodiments for making the compositions of the present disclosure are provided in Examples 1-3.

As described herein, appropriate water-soluble polystyrenes and salts thereof have been found to unexpectedly provide unique and surprising effects in the preparation of the compositions provided herein. For instance, the use of water-soluble polystyrenes and salts thereof with appropriate molecular weight in the methods described herein is critical in preparing the liquid to semi-solid compositions as described herein (e.g., containing at least one alpha-hydroxy acid combined with at least one beta-hydroxy acid) that are essentially homogeneous and stable. Further, the compositions prepared by the methods described herein can remain homogeneous and stable even under prolonged storage, and at the same time are effective for the treatment of the various skin conditions and disorders.

The compositions provided herein can be used in various methods of improving a skin condition in a subject in need thereof. The skin conditions that can be improved by the compositions provided herein include, inter alia, aging, color, texture of the skin. For example, the compositions provided herein may be used to rejuvenate the appearance of the skin, i.e., to make the skin look younger. In other examples, the compositions provided herein may be used to even discoloration of the skin, e.g., to reduce dark spots. In yet other examples, the compositions provided herein may be used to smooth the texture of the skin, to reduce wrinkles, to make the skin more elastic, or to reduce the pore size of the skin.

Generally, a method of improving a skin condition provided herein involves applying the composition of the present disclosure on an area of the skin in need thereof. Some non-limiting exemplary uses for the composition in accordance to this disclosure include cosmetic use by humans. Without being limiting, cosmetic uses encompass the application of the composition on skin (including the entire body such as face, scalp, neck, decolletée, arms, legs, torso, back, hands, feet, heels, and genital skin) to cleanse, beautify, smooth, exfoliate, rejuvenate, refine pores, open clogged pores, enhance tone, brighten, lighten, help loosen ingrown hair, and other related or unrelated cosmetic purposes. Other uses include the treatments of multiple skin disorders including, but not limited to, acne, folliculitis or pseudo-folliculitis, seborrheic dermatitis, rosacea, hyperkeratosis, actinic keratosis, and skin cancers (such as squamous or basal cell carcinoma). Further, the composition in accordance to this disclosure can also be used for the treatment of hair, dandruff, hair loss, and nails of finger and toes.

While an important use for the composition in accordance to this disclosure is for human use, the compositions provided herein are also well suited to be used in animals, such as without being limited to cats, dogs, horses, sheep, pigs, and cattle in need thereof.

EXAMPLES

Example 1: Composition A

Composition A is an example of a composition in accordance to the present disclosure. This Example illustrates the process that was used to make Composition A. Composition A was prepared as follows:

Part 1: In a first appropriate container (e.g., mixing vessel, glass beaker, etc.) depending on batch size (total 500 g in this example) which is kept at room temperature (between approximately 20° C. to 30° C.) during the preparation of this composition, place 180.5 g water (36.1%) and then add 107 g of 70% Glycolic Acid (21.4% of 70% Glycolic Acid; corresponding to 15% Glycolic Acid) under gentle mixing. After getting a uniform mixture, add 37.5 g (corresponding to 7.5% (w/w) in the final composition) sodium polystyrene sulfonate (FLEXAN® II Polymer supplied by AkzoNobel) under mixing until fully dissolved.

Part 2: In a second appropriate container (e.g., mixing vessel, glass beaker, etc.) depending on batch size (total 500 g in this example) which is kept at room temperature (between approximately 20° C. to 30° C.) during the preparation of this composition, place 150.0 g of Ethanol 200 proof (corresponding to 30.0% (w/w) ethyl alcohol in the final composition) and then add 25.0 g of Salicylic Acid (corresponding to 5.0% (w/w) in the final composition) under mixing. Mix until a uniform mixture is obtained.

Thereafter, slowly add Part 1 to Part 2 under continuous mixing until a uniform mixture is obtained; mix for an additional about 5 to 10 minutes, and then check the pH of the final composition (Composition A). The final water content of this composition is 42.5%. The pH of this composition is between 1.5 to 2.5 when measured at about 25° C.

Composition A presents as a clear to slightly opaque, yellowish to brownish, and homogeneous liquid. The composition remains stable (i.e., appearance, pH range, homogeneity, viscosity) over a prolonged period of time (i.e., at least for 2 years) when kept in an appropriate closed container (e.g., plastic jar, plastic bottle, special glass container, cosmetic dispenser, . . . ) under normal storage condition typical for cosmetic and/or dermatology products (e.g., kept at room temperature, kept in bathroom at home, kept in skin care/medical cabinet, etc.). Since the pH of Composition A is low (below a pH of about 3.0) and also remains low (below a pH of about 3.0) during storage (i.e., during the shelf-life of the product), Composition A is effective for the treatment of the various skin conditions as disclosed in this disclosure.

Instead of Ethanol 200 proof, denatured ethyl alcohol can be used. The ingredients ethyl alcohol, glycolic acid (e.g., 70% glycolic acid), and salicylic acid can be obtained from any supplier of raw materials for the cosmetic and pharmaceutical industry. They should be of sufficient high quality and purity for cosmetic and/or pharmaceutical uses.

The same composition without the sodium polystyrene sulfonate (i.e., FLEXAN® II Polymer) in which the sodium polystyrene sulfonate is replaced with water is not stable, homogeneous, and at the same time, also of low pH (e.g., below a pH of about 3.0) and therefore effective. Such a composition is not in accordance with the present disclosure. Similarly, the same composition without the sodium polystyrene sulfonate (i.e., FLEXAN® II Polymer) in which the sodium polystyrene sulfonate is replaced with a water-soluble non-polystyrene polymer (e.g., polyethylene glycol, polypropylene glycol, hyaluronic acid, etc.) is not stable, homogeneous, and at the same time, also of low pH (e.g., below a pH of about 3.0) and therefore effective. Such a composition is also not in accordance to the present disclosure.

Example 2: COMPOSITION B

Composition B is another example of a composition in accordance to the present disclosure. This Example illustrates the process that was used to make Composition B. Composition B was prepared as follows:

Part 1: In a first appropriate container (e.g., mixing vessel, glass beaker, etc.) depending on batch size (total 500 g in this example) which is kept at room temperature (between approximately 20° C. to 30° C.) during the preparation of this composition, place 191.4 g water (38.28%) and then add 53.5 g of 70% Glycolic Acid (10.7% of 70% Glycolic Acid; corresponding to 7.5% Glycolic Acid) and 42.6 g of 88% Lactic Acid (8.52% of 88% Lactic Acid; corresponding to 7.5% Lactic Acid) under gentle mixing. After getting a uniform mixture, add 37.5 g (corresponding to 7.5% (w/w) in the final composition) sodium polystyrene sulfonate (FLEXAN® II Polymer supplied by AkzoNobel) under mixing until fully dissolved.

Part 2: In a second appropriate container (e.g., mixing vessel, glass beaker, etc.) depending on batch size (total 500 g in this example) which is kept at room temperature (between approximately 20° C. to 30° C.) during the preparation of this composition, place 150.0 g of Ethanol 200 proof (corresponding to 30.0% (w/w) ethyl alcohol in the final composition) and then add 25.0 g of Salicylic Acid (corresponding to 5.0% (w/w) in the final composition) under mixing. Mix until a uniform mixture is obtained.

Thereafter, slowly add Part 1 to Part 2 under continuous mixing until a uniform mixture is obtained; mix for an additional about 5 to 10 minutes, and then check the pH of the final composition (Composition B). The final water content of this composition is 42.5%. The pH of this composition is between 1.5 to 2.5 when measured at about 25° C.

Composition B presents as a clear to slightly opaque, yellowish to brownish, and homogeneous liquid. The composition remains stable (i.e., appearance, pH range, homogeneity, viscosity) over a prolonged period of time (i.e., at least for 2 years) when kept in an appropriate closed container (e.g., plastic jar, plastic bottle, special glass container, cosmetic dispenser, . . . ) under normal storage condition typical for cosmetic and/or dermatology products (e.g., kept at room temperature, kept in bathroom at home, kept in skin care/medical cabinet, etc.). Since the pH of Composition B is low (below a pH of about 3.0) and also remains low (below a pH of about 3.0) during storage (i.e., during the shelf-life of the product), Composition B is effective for the treatment of the various skin conditions as disclosed in this disclosure.

Instead of Ethanol 200 proof, denatured ethyl alcohol can be used. The ingredients ethyl alcohol, glycolic acid (e.g., 70% glycolic acid), lactic acid (e.g., 88% lactic acid), and salicylic acid can be obtained from any supplier of raw materials for the cosmetic and pharmaceutical industry. They should be of sufficient high quality and purity for cosmetic and/or pharmaceutical uses.

The same composition without the sodium polystyrene sulfonate (i.e., FLEXAN® II Polymer) where the sodium polystyrene sulfonate is replaced with water is not stable, homogeneous, and at the same time, also of low pH (below a pH of about 3.0) and therefore effective. Such a composition is not in accordance to the present disclosure. Similarly, the same composition without the sodium polystyrene sulfonate (i.e., FLEXAN® II Polymer) where the sodium polystyrene sulfonate is replaced with a water-soluble non-polystyrene polymer (e.g., polyethylene glycol, polypropylene glycol, hyaluronic acid, etc.) is not stable, homogeneous, and at the same time, also of low pH (below a pH of about 3.0) and therefore effective. Such a composition is also not in accordance to the present disclosure.

Example 3: COMPOSITION C

Composition C is yet another example of a composition in accordance to the present disclosure. This Example illustrates the process that was used to make Composition C. Composition C was prepared as follows:

Part 1: In a first appropriate container (e.g., mixing vessel, glass beaker, etc.) depending on batch size (total 500 g in this example) which is kept at room temperature (between approximately 20° C. to 30° C.) during the preparation of this composition, place 175.5 g water (35.1%) and then add 107 g of 70% Glycolic Acid (21.4% of 70% Glycolic Acid; corresponding to 15% Glycolic Acid) under gentle mixing. After getting a uniform mixture, add 37.5 g (corresponding to 7.5% (w/w) in the final composition) sodium polystyrene sulfonate (FLEXAN® II Polymer supplied by AkzoNobel) under mixing until fully dissolved.

Part 2: In a second appropriate container (e.g., mixing vessel, glass beaker, etc.) depending on batch size (total 500 g in this example) which is kept at room temperature (between approximately 20° C. to 30° C.) during the preparation of this composition, place 150.0 g of Ethanol 200 proof (corresponding to 30.0% (w/w) ethyl alcohol in the final composition) and then add 25.0 g of Salicylic Acid (corresponding to 5.0% (w/w) in the final composition) under mixing mix until a uniform mixture is obtained. Then, add 5 g (1%) of Kojic Acid under mixing until fully dissolved.

Thereafter, slowly add Part 1 to Part 2 under continuous mixing until a uniform mixture is obtained; mix for an additional about 5 to 10 minutes, and then check the pH of the final composition (Composition C). The final water content of this composition is 41.5%. The pH of this composition is between 1.5 to 2.5 when measured at about 25° C.

Composition C presents as a clear to slightly opaque, yellowish to brownish, and homogeneous liquid. The composition remains stable (i.e., appearance, pH range, homogeneity, viscosity) over a prolonged period of time (i.e., at least for 2 years) when kept in an appropriate closed container (e.g., plastic jar, plastic bottle, special glass container, cosmetic dispenser, . . . ) under normal storage condition typical for cosmetic and/or dermatology products (e.g., kept at room temperature, kept in bathroom at home, kept in skin care/medical cabinet, etc.). Since the pH of Composition C is low (below a pH of about 3.0) and also remains low (below a pH of about 3.0) during storage (i.e., during the shelf-life of the product), Composition C is effective for the treatment of the various skin conditions as disclosed in this disclosure.

Instead of Ethanol 200 proof, denatured ethyl alcohol can be used. The ingredients ethyl alcohol, glycolic acid (e.g., 70% glycolic acid), salicylic acid, and kojic acid can be obtained from any supplier of raw materials for the cosmetic and pharmaceutical industry. They should be of sufficient high quality and purity for cosmetic and/or pharmaceutical uses.

This example illustrates the addition of one or more additional actives. In the present example, the skin brightening agent Kojic Acid is added. Other examples of suitable skin brightening actives include but are not limited to aloesin, azelaic acid, arbutin, deoxy-arbutin, ascorbic acid, glabridin, resorcinol, phenylethyl resorcinol, 4-n-butyl resorcinol, resveratrol, oxyresveratrol, hydroquinone, tranexamic acid, niacinamide, retinol, retinaldehyde, retinoic acid, tretinoin, undecylenoyl phenylalanine, licorice extract, mulberry leaf extract, Moms alba leaf extract, lichochalcone A, bearberry extract, trichloroacetic acid, phenol, quercetin, mequinol, cysteamine, melatonin, glutathione, soybean extract, and more as known by a skilled person in the art.

The same composition without the sodium polystyrene sulfonate (i.e., FLEXAN® II Polymer) where the sodium polystyrene sulfonate is replaced with water is not stable, homogeneous, and at the same time, also of low pH (below a pH of about 3.0) and therefore effective. Such a composition is not in accordance to the present disclosure. Similarly, the same composition without the sodium polystyrene sulfonate (i.e., FLEXAN® II Polymer) where the sodium polystyrene sulfonate is replaced with a water-soluble non-polystyrene polymer (e.g., polyethylene glycol, polypropylene glycol, hyaluronic acid, etc.) is not stable, homogeneous, and at the same time, also of low pH (below a pH of about 3.0) and therefore effective. Such a composition is also not in accordance to the present disclosure.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A composition comprising at least one alpha-hydroxy acid, at least one beta-hydroxy acid, and one or more water-soluble polystyrene or a salt thereof, wherein the concentration of the at least one alpha-hydroxy acid is at least about 5% (w/w) to about 40% (w/w/) and the concentration of the at least one beta-hydroxy acid is at least about 2% (w/w/) to about 25% (w/w), wherein the one or more water-soluble polystyrene or a salt thereof has a molecular weight in the range of about 10,000 to about 1,000,000 g/mol, wherein the composition has a pH of about 3.5 or lower, and wherein the composition is a homogeneous liquid.

2. The composition of claim 1, wherein the at least one alpha-hydroxy acid comprises 2-hydroxyoctanoic acid, 2-hydroxydecanoic acid, citric acid, glycolic acid, gluconic acid, lactic acid, malic acid, mandelic acid, tartaric acid, or a salt thereof.

3. The composition of claim 1, wherein the at least one beta-hydroxy acid comprises salicylic acid, beta-hydroxybutanoic acid, tropic acid, trethocanic acid, and 5-(n-octanoyl) salicylic acid.

4. The composition of claim 1, wherein the one or more water-soluble polystyrene or a salt thereof comprises an anionic polystyrene and a cationic polystyrene.

5. The composition of claim 1, wherein the concentration of the one or more water-soluble polystyrene or a salt thereof is in the range of about 0.1% to about 35% (w/w).

6. The composition of claim 1, further comprises ethyl alcohol and water.

7. The composition of claim 1, further comprising at least one additional hydroxy acid or a salt thereof.

8. The composition of claim 7, wherein the at least one additional hydroxy acid or a salt thereof comprises an alpha-hydroxy acid or a salt thereof, at least one beta-hydroxy acid or a salt thereof, or a polyhydroxy acid or a salt thereof.

9. The composition of claim 1, further comprising an ascorbic acid.

10. The composition of claim 1, further comprising a non-hydroxy acid.

11. The composition of claim 1, comprising (i) about 15% (w/w) of glycolic acid, about 5% (w/w) of salicylic acid, and about 7.5% (w/w) sodium polystyrene sulfonate, wherein the composition has a pH of about 3.0 or lower; (ii) about 7.5% (w/w) of glycolic acid, about 7.5% (w/w) of lactic acid, about 5% (w/w) of salicylic acid, and about 7.5% (w/w) sodium polystyrene sulfonate, wherein the composition has a pH of about 3.0 or lower; or (iii) about 15% (w/w) of glycolic acid, about 5% (w/w) of salicylic acid, about 1% (w/w) of kojic acid, and about 7.5% (w/w) sodium polystyrene sulfonate, wherein the composition has a pH of about 3.0 or lower.

12. A method of making the composition of claim 1, comprising combining at least one alpha-hydroxy acid and at least one beta-hydroxy acid in the presence of one or more water-soluble polystyrene or a salt thereof, and wherein the presence of the one or more water-soluble polystyrene or a salt thereof allows the at least one alpha-hydroxy acid and the at least one beta-hydroxy acid to be combined in one homogeneous composition suitable for topical use.

13. The method of claim 12, further comprising combining the at least one alpha-hydroxy and the one or more water-soluble polystyrene or a salt thereof prior to combining the at least one alpha-hydroxy acid and the at least one beta-hydroxy acid.

14. A method of improving a skin condition in a subject in need thereof comprising applying the composition of claim 1 on an area of the skin.

15. The method of claim 14, wherein the skin condition comprises aging, color, texture of the skin, acne, folliculitis or pseudo-folliculitis, seborrheic dermatitis, rosacea, hyperkeratosis, actinic keratosis, and a skin cancer.

* * * * *